United States Patent [19]

Jelich

[11] Patent Number: 5,116,993
[45] Date of Patent: May 26, 1992

[54] PROCESS FOR THE PREPARATION OF 2-CHLORO-5-CHLOROMETHYLPYRIDINE, AND NEW INTERMEDIATES

[75] Inventor: Klaus Jelich, Wuppertal, Fed. Rep. of Germany

[73] Assignee: Bayer Aktiengesellschaft, Leverkusen, Fed. Rep. of Germany

[21] Appl. No.: 759,702

[22] Filed: Sep. 11, 1991

Related U.S. Application Data

[63] Continuation of Ser. No. 504,783, Apr. 4, 1990, abandoned.

[30] Foreign Application Priority Data

Apr. 20, 1989 [DE] Fed. Rep. of Germany ....... 3912964

[51] Int. Cl.$^5$ .......................................... C07D 213/61
[52] U.S. Cl. .................................... 546/345
[58] Field of Search ..................... 546/345

[56] References Cited

U.S. PATENT DOCUMENTS 4,576,629  3/1986  Morland et al. ................. 70/90

FOREIGN PATENT DOCUMENTS 0009212  4/1980  European Pat. Off. .
0065358  11/1982  European Pat. Off. .
0163855  12/1985  European Pat. Off. .
3630046  3/1988  Fed. Rep. of Germany .

OTHER PUBLICATIONS

Snythesis of Heterocyclic Analogs of Methyldopa, J. W. Tilley et al., J. Heterocyclic Chem., 16, 333 (1979).
A Novel Transformation of 3-Alkoxyisoquinolines to 3-chloroisoquinolines and an unusual decyanation of 1,3-dialkoxy-4-cyano-5,6,7,8-tetrahydroisoquinolines under vilsmeier-Haack conditions, T. R. Kasturi et al., Synthesis, 1984, 743-745.

*Primary Examiner*—Paticia L. Morris
*Assistant Examiner*—Lenora Miltenberger
*Attorney, Agent, or Firm*—Sprung, Horn, Kramer & Woods

[57] ABSTRACT

A process for the preparation of a 2-chloro-5-chloromethyl-pyridine, of the formula (I)

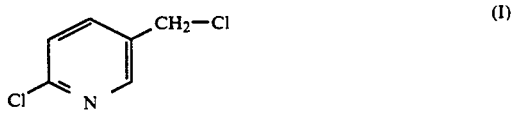

comprising reacting a 2-alkoxy-5-alkoxymethylpyridine derivative of the formula (II)

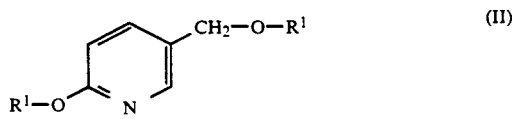

in which
  $R^1$ represents alkyl,
with a chlorinating agent, is appropriate, in the presence of a diluent and if appropriate, in the presence of a reaction auxiliary, at a temperature between 0° C. and 200° C.

9 Claims, No Drawings

PROCESS FOR THE PREPARATION OF 2-CHLORO-5-CHLOROMETHYLPYRIDINE, AND NEW INTERMEDIATES

This application is a continuation of application Ser. No. 504,783, filed Apr. 4, 1990, abandoned.

The invention relates to a new process for the preparation of 2-chloro-5-chloromethyl-pyridine, which is known as an intermediate for insecticides, to new intermediates for this process, and to a process for their preparation.

It is known that 2-chloro-5-chloromethylpyridine is obtained in a complicated multi-step process when 2-chloropyridine-5-carboxylic acid is converted with thionyl chloride into the corresponding acid chloride; if appropriate, the latter is esterified with ethanol, then reduced with sodium boranate to give the hydroxymethyl compound, and the hydroxyl group in the side chain is finally substituted by chlorine using thionyl chloride (cf., for example, U.S. Pat. No. 4,576,629; J. Heterocycl. Chem. 16, 333–337 [1979]).

The disadvantage of this process, and what is prohibitive with regard to large-scale feasibility, is the high price of the starting compound 2-chloropyridine-5carboxylic acid and of the reducing agent sodium boranate, which, furthermore, also presents a safety problem with respect to the liberation of hydrogen during the course of the reaction.

Furthermore, it is known that 2-chloro-5-chloromethylpyridine is obtained when 2-chloro-5-methylpyridine is reacted with elemental chlorine (cf., for example, DE-A 3,630,046). However, the disadvantage in this process is that the reaction does not proceed uniformly, which makes it necessary to interrupt the chlorination at an early stage, before the reaction could have proceeded to completion, in order to avoid the formation of substantial amounts of polychlorinated by-products (cf. also EP-A 9,212; EP-A 65,358). The resulting mixtures can only be separated with difficulty and give products whose purity is unsatisfactory.

It has now been found that 2-chloro-5-chloromethylpyridine, of the formula (I),

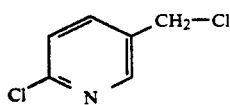

is obtained when 2-alkoxy-5-alkoxymethyl-pyridine derivatives of the general formula (II)

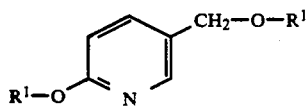

in which
R$^1$ represents alkyl, are reacted with a chlorinating agent, if appropriate in the presence of a diluent and if appropriate in the presence of a reaction auxiliary, at temperatures between 0° C. and 200° C.

It is surprising that the reaction of 2-alkoxy-5-alkoxymethyl-pyridine derivatives of the formula (II) with chlorinating agents according to the process according to the invention leads to an exchange of both alkoxy groups against chlorine, since it was known from the prior art that "Vilsmeier-Haack conditions" (that is to say phosphorus oxychloride in the presence of large amounts of dimethylformamide, with considerable amounts of waste water being produced during working-up), which are not very suitable for large-scale industrial production, would be required for converting 2-methoxypyridine into 2-chloropyridine, phosphorus oxychloride in the absence of dimethylformamide not effecting any kind of reaction. Furthermore, with less than 40% yield, this reaction gives only a highly contaminated product which must be subjected to complicated purification by chromatography (cf. in this context, Synthesis 1984, 743–745).

Advantages of the process according to the invention are that the 2-alkoxy-5-alkoxymethyl-pyridine derivatives (II) which are used as starting compounds are readily accessible, that the total number of synthesis steps is low, and that inexpensive chemicals for synthesis are employed in the preparation of (II), it being possible for the inexpensive chemical 3-methylpyridine to be employed as the basic compound.

If, for example, 2-methoxy-5-methoxymethylpyridine and phosphorus(V) chloride are used as the starting substances, the course of the reaction in the process according to the invention can be outlined by the following equation:

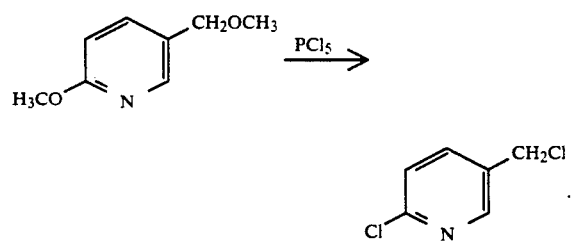

Formula (II) provides a general definition of the 2-alkoxy-5-alkoxymethyl-pyridine derivatives to be used as starting substances. R$^1$ in formula (II) represents straight-chain or branched alkyl, preferably having 1 to 6, in particular having 1 to 4, carbon atoms.

Examples which may be mentioned of the starting substances of the formula (II) are:
2-methoxy-5-methoxymethyl-pyridine, 2-ethoxy-5-ethoxymethyl-pyridine, 2-propoxy-5-propoxymethyl-pyridine, 2-isopropoxy-5-isopropoxymethyl-pyridine, 2-butoxy5-butoxymethyl-pyridine, 2-isobutoxy-5-isobutoxymethylpyridine, 2-sec-butoxy-5-sec-butoxymethyl-pyridine and 2-tert-butoxy-5-tert-butoxymethyl-pyridine.

The starting substances of the formula (II) were hitherto unknown. The new 2-alkoxy-5-alkoxymethyl-pyridine derivatives of the formula (II) are obtained when 3-dichloromethyl-pyridine, of the formula (III),

is reacted with an alcohol of the formula (IV)

R$^1$OH  (IV)

where R¹ has the abovementioned meaning, and with alkali metal salts of alcohols of the formula (IV) at temperatures between 0° C. and 150° C., preferably between 20° C. and 100° C., and the product is worked up by customary methods. For example, the reaction mixture is concentrated after the reaction; after cooling, the concentrate is stirred with organic solvents (e.g., ether), salts are separated by filtration with suction, and the filtrate is concentrated. The residue is then purified by customary methods, for example, by chromatography.

No model is known from the field of pyridine derivative chemistry for the above-described route for the preparation of the new 2-alkoxy-5-alkoxymethyl-pyridine derivatives. It is therefore surprising that 2-alkoxy-5-alkoxymethyl-pyridines can be prepared from 3-dichloromethyl-pyridine and alkoxides.

3-Dichloromethylpyridine, which has the formula (III) and is required as an intermediate, is already known (cf. EP-A 9,212 and EP-A 65,358), but it is generally obtained as a by-product in the chlorination of 3-methylpyridine.

Moreover, it has been found that 3-dichloromethyl-pyridine, of the formula (III), is obtained in good yields as the main product when 3-methylpyridine, of the formula (V),

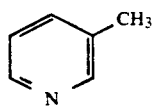

is reacted with elemental chlorine in the presence of an organic acid, such as, for example, acetic acid, propionic acid, chloroacetic acid, dichloroacetic acid, trichloroacetic acid, trifluoroacetic acid, methanesulphonic acid and/or trifluoromethanesulphonic acid (preferably acetic acid) and if appropriate additionally in the presence of an inorganic acid, such as, for example, hydrogen chloride, hydrogen bromide or sulphuric acid (preferably sulphuric acid), and also in the presence of a free-radical initiator, such as, for example, azo-bisisobutyronitrile, benzoyl peroxide or tert-butyl perbenisobutyro zoate, at temperatures between −20° C. and +150° C., preferably between 0° C. and 100° C., and the reaction product is worked up by customary methods, for example by taking it up in a suitable organic solvent, such as, for example, ethyl acetate, neutralizing the solution with an alkali (for example NaOH), separating off the organic phase, drying the organic phase and distilling off the solvent.

With a view to the prior art (where compound (III) is obtained only as a by-product), the selective course of the process described above is considered as extremely surprising.

Formula (IV) provides a general definition of the alcohols furthermore required as starting substances. R¹ in formula (IV) represents a straight-chain or branched alkyl, preferably having 1 to 6, in particular having 1 to 4, carbon atoms.

In the preparation of compounds of the formula (II), it is preferred to employ the lithium, sodium or potassium salts, in particular the sodium salts, of these alcohols.

Examples which may be mentioned are: methanol, ethanol, propanol, isopropanol, butanol, isobutanol, secbutanol and tert-butanol, and also the sodium salts of these alcohols.

Chlorinating agents which are preferably suitable for the preparation of 2-chloro-5-chloromethyl-pyridine, of the formula (I), from 2-alkoxy-5-alkoxymethyl-pyridine derivatives of the formula (II) by the process according to the invention are inorganic or organic acid chlorides, such as, for example, phosphorus(V) chloride, phosphorus(III) chloride, phosphoryl chloride (phosphorus oxychloride), thionyl chloride, phosgene, acetyl chloride or benzotrichloride, in particular mixtures of phosphorus(V) chloride and phosphoryl chloride.

The process according to the invention can be carried out either without the addition of a diluent, in substance, or in the presence of a suitable diluent. These include, in particular, aliphatic, alicyclic or aromatic, optionally halogenated hydrocarbons, such as, for example, benzene, toluene, xylenes, chlorobenzene, dichlorobenzenes, petroleum ether, hexane, cyclohexane, methylcyclohexane, dichloromethane, chloroform or tetrachloromethane.

If appropriate, the process according to the invention can be carried out in the presence of a suitable reaction auxiliary. Possible reaction auxiliaries are tertiary amines, such as triethylamine, N,N-dimethylaniline, pyridine or 4-dimethylamino-pyridine, and furthermore also catalytic amounts of formamides, such as N,N-dimethyl-formamide or N,N-dibutylformamide, or metal halides, such as magnesium chloride or lithium chloride.

When carrying out the process according to the invention, the reaction temperatures can be varied within a substantial range. In general, the process is carried out at temperatures between 0° C. and 200° C., preferably between 10° C. and 120° C.

For carrying out the process according to the invention, between 1 and 10 mole equivalents, preferably between 1 and 5 mole equivalents, of the chlorinating agent are generally employed per mole of 2-alkoxy-5-alkoxymethyl-pyridine derivative of the formula (II).

In general, the reactants are combined with gentle cooling and then stirred until the reaction is complete, in general at a slightly elevated temperature. The reaction product is worked up by customary methods (cf. Preparation Examples).

2-Chloro-5-chloromethyl-pyridine, which has the formula (I) and can be obtained by the process according to the invention, can be used as an intermediate in the preparation of insecticides, (cf. EP-A 163,855 and EP-A 192,060).

PREPARATION EXAMPLES

Example 1

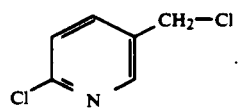

To 5.1 g (33.3 mmol) of phosphorus oxychloride there are first added 14 g (66.6 mmol) of phosphorus(V) chloride and then, with cooling in an ice-bath, 5.1 g (33.3 mmol) of 2-methoxy-5-methoxymethyl-pyridine in portions. The reaction mixture is refluxed for 3 hours and then concentrated in vacuo. The residue is diluted with ice-water, the mixture is rendered neutral with 2N sodium hydroxide solution, and shaken with ethyl acetate. The organic phase is separated off, dried with sodium sulphate and filtered. The solvent is removed from the filtrate by distillation under a waterpump vacuum. This gives 2.4 g (45% of theory) of 2-chloro-5-chloromethylpyridine as the residue (yellow liquid).

STARTING SUBSTANCES OF THE FORMULA (II)

Example (II-1)

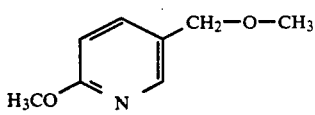

A solution of 35.8 g (73% pure; 0.161 mol) of 3-dichloromethyl-pyridine in 50 ml of methanol is added dropwise to a refluxed solution of 29.5 g (0.55 mol) of sodium methoxide in 90 ml of methanol. The reaction mixture is refluxed for 4 more hours and then concentrated.

The residue is stirred with diethyl ether, sodium chloride which has remained undissolved is separated off by filtration with suction, and the filtrate is concentrated. The residue is purified by chromatography on silica gel (eluent: petroleum ether/ethyl acetate, 5:1 by volume).

This gives 12.3 g (50% of theory) of 2-methoxy-5-methoxymethyl-pyridine.

$^1$H-NMR (CDCl$_3$, δ, ppm): 2.8; 3.9; 4.4.

The following are obtained analogously:

Example (II-2)

The compound

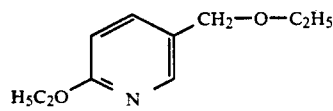

from 3-dichloromethylpyridine with sodium ethoxide and ethanol $^1$H-NMR (CDCl$_3$, δ, ppm): 3.5; 4.3; 4.4.

Example (II-31)

The compound

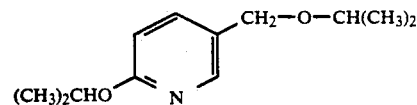

from 3-dichloromethylpyridine with sodium isopropoxide and isopropanol $^1$H-NMR (CDCl$_3$, δ, ppm): 4.4.

Example (II-4)

The compound

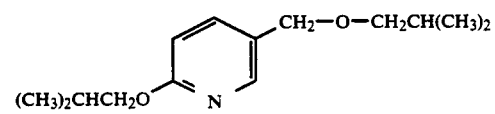

from 3-dichloromethylpyridine with sodium isobutoxide and isobutanol $^1$H-NMR (CDCl$_3$), δ, ppm): 3.2; 4.05; 4.4.

STARTING COMPOUND OF THE FORMULATE (III)

Example (III-1)

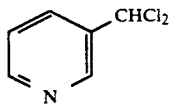

23.3 g (0.25 mol) of 3-methylpyridine are added dropwise with stirring to a mixture, cooled in an icebath, of 25 g (0.255 mol) of concentrated sulphuric acid and 150 ml of acetic acid. The reaction mixture is heated to 75° C., and a solution of 4.0 g of azo-bisisobutyronitrile in 30 ml of glacial acetic acid is added dropwise in the course of 8 hours, with a vigorous stream of chlorine being passed through. After the mixture has been concentrated, the residue is taken up in ethyl acetate and rendered neutral using 2N sodium hydroxide solution. The organic phase is filtered off with suction, dried with sodium sulphate and filtered. The solvent is removed from the filtrate by distillation under a waterpump vacuum. This gives 41 g (73% of theory, 79% pure) of 3-dichloromethyl-pyridine as the residue (yellow liquid).

It will be appreciated that the instant specification is set forth by way of illustration and not limitation, and that various modifications and changes may be made without departing from the spirit and scope of the present invention.

What is claimed is:

1. A process for the preparation of 2-chloro-5-chloromethyl-pyridine of the

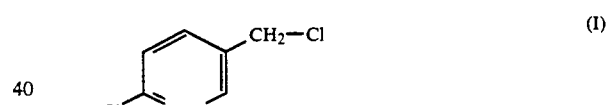

comprising reacting a 2-alkoxy-5-alkoxymethylpyridine derivative of the formula (II)

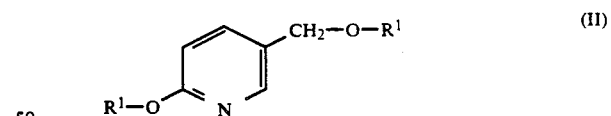

in which

R$^1$ represents alkyl, with a chlorination agent selected from the group consisting of phosphorous (V) chloride, phosphorus (III) chloride, and phosphoryl chloride, at a temperature between 0° C. and 200° C., optionally in the presence of a reaction auxiliary excluding DMF.

2. A process according to claim 1, wherein the chlorinating agent is an inorganic or organic acid chloride.

3. A process according to claim 1, wherein the diluent is a halogenated hydrocarbon.

4. A process according to claim 1, wherein 1 and 10 mole equivalents of the chlorinating agent are employed per mole of the 2-alkoxy-5-alkoxymethylpyridine derivative of the formula (II).

5. A process according to claim 1, wherein 1 to 5 mole equivalents of the chlorinating agent are employed per mole of the 2-alkoxy-5-alkoxymethylpyridine derivative of the formula (II).

6. A process according to claim 1, wherein $R^1$ is a straight-chain or branched alkyl having 1 to 6 carbon atoms.

7. A process according to claim 1, further comprising conducting the process in the presence of a reaction auxiliary excluding DMF.

8. A process according to claim 7, wherein the reaction auxiliary is a tertiary amine, or a metal halide.

9. A process according to claim 1, wherein the process is carried out at a temperature between 10° C. and 120° C.

* * * * *

UNITED STATES PATENT AND TRADEMARK OFFICE
CERTIFICATE OF CORRECTION

PATENT NO. : 5,116,993

DATED : May 26, 1992

INVENTOR(S) : Klaus Jelich

It is certified that error appears in the above-identified patent and that said Letters Patent is hereby corrected as shown below:

Col. 6, line 35  After " of the " insert -- formula (I) --

Signed and Sealed this

Twentieth Day of August, 1996

Attest:

BRUCE LEHMAN

*Attesting Officer*  *Commissioner of Patents and Trademarks*